(12) United States Patent
Rijkx

(10) Patent No.: US 8,343,732 B2
(45) Date of Patent: Jan. 1, 2013

(54) METHOD FOR DETERMINING TYPES OF CELLS

(75) Inventor: Joseph Maria Franciscus Donatus Rijkx, Nuth (NL)

(73) Assignee: Amiris B.V., Sittard (NL)

( * ) Notice: Subject to any disclaimer, the term of this patent is extended or adjusted under 35 U.S.C. 154(b) by 31 days.

(21) Appl. No.: 12/094,893

(22) PCT Filed: Nov. 23, 2006

(86) PCT No.: PCT/NL2006/000590
§ 371 (c)(1),
(2), (4) Date: May 23, 2008

(87) PCT Pub. No.: WO2007/061293
PCT Pub. Date: May 31, 2007

(65) Prior Publication Data
US 2008/0293078 A1 Nov. 27, 2008

(30) Foreign Application Priority Data
Nov. 25, 2005 (NL) .................................... 1030525

(51) Int. Cl.
*C12Q 1/04* (2006.01)
(52) U.S. Cl. ........................................................ 435/34
(58) Field of Classification Search .................. 435/34, 435/8, 31
See application file for complete search history.

(56) References Cited

U.S. PATENT DOCUMENTS

| | | | |
|---|---|---|---|
| 5,736,351 A * | 4/1998 | Miller et al. ........................ | 435/8 |
| 5,891,702 A * | 4/1999 | Sakakibara et al. ........... | 435/227 |
| 6,200,767 B1 * | 3/2001 | Sakakibara et al. .............. | 435/8 |
| 6,569,637 B1 | 5/2003 | Aoyagi et al. | |
| 6,951,723 B2 | 10/2005 | Crouch et al. | |
| 2006/0263773 A1 * | 11/2006 | Tanaka .............................. | 435/6 |

FOREIGN PATENT DOCUMENTS

| | | |
|---|---|---|
| CH | 678065 | 7/1991 |
| EP | 0025351 | 3/1981 |
| WO | WO 2006/085972 A2 | 8/2006 |

OTHER PUBLICATIONS

Schram E. et al. Improved ATP Methodology for Biomass Assays. J of Bioluminescence and Chemiluminescence 4:390-398, 1989.*
Gorus F. et al. Applications of Bio and Chemiluminescence in the Clinical Laboratory. Clinical Chemistry 25(4)512-518, 1979.*
Lundin et al. Substrate and Enzyme Determinations by Continuously Monitoring the ATP Level by a Purified Luciferase Reagent. ATP Methodology Symposium Proceedings. 1977 San Diego 205-218.*
Lundin A. et al. Continuous Monitoring of ATP Converting Reactions by Purified Firefly Luciferase. Analytical Biochemstry 75:611-620, 1976.*
International Search Report for PCT International Application No. PCT/NL2006/000590, mailed Apr. 5, 2007 (3 pgs.).
Schram E. et al., "Improved ATP Methodology for Biomass Assays.", *Journal of Bioluminescence and Chemiluminescence*, vol. 4, No. 1, 1989, pp. 390-398. (XP002386929).
Office Action received in the related European Patent Application 06 824 280.9, dated Feb. 19, 2009.
Office Action and International Preliminary Report on Patentability received in the related European Patent Application 06 824 280.9, dated Sep. 11, 2009.
Office Action received in the related European Patent Application 06 824 280.9, dated Dec. 8, 2009.
Minutes of the Oral Proceedings received in related European Application No. 06824280.9, mailed Jun. 21, 2010.

* cited by examiner

*Primary Examiner* — Ralph Gitomer
(74) *Attorney, Agent, or Firm* — Foley & Lardner LLP

(57) ABSTRACT

The present invention relates to a method for detecting ATP in a sample by using luminescence, wherein a luminescence reagent is added to the sample that has not undergone any pre-treatment with an extractant in order to effect the formation of an ATP complex, wherein the luminescence of the ATP complex thus formed is measured.

10 Claims, 13 Drawing Sheets

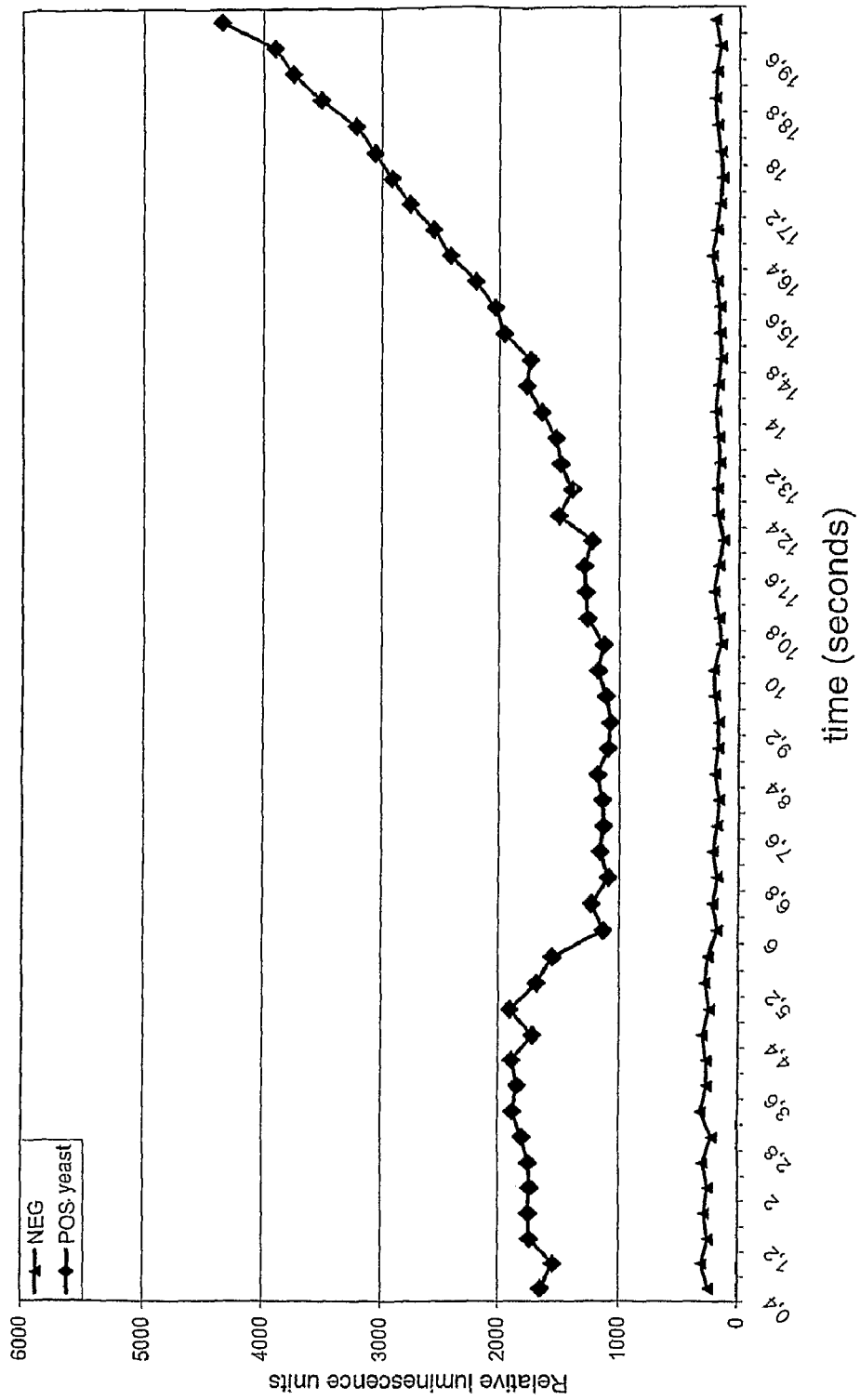

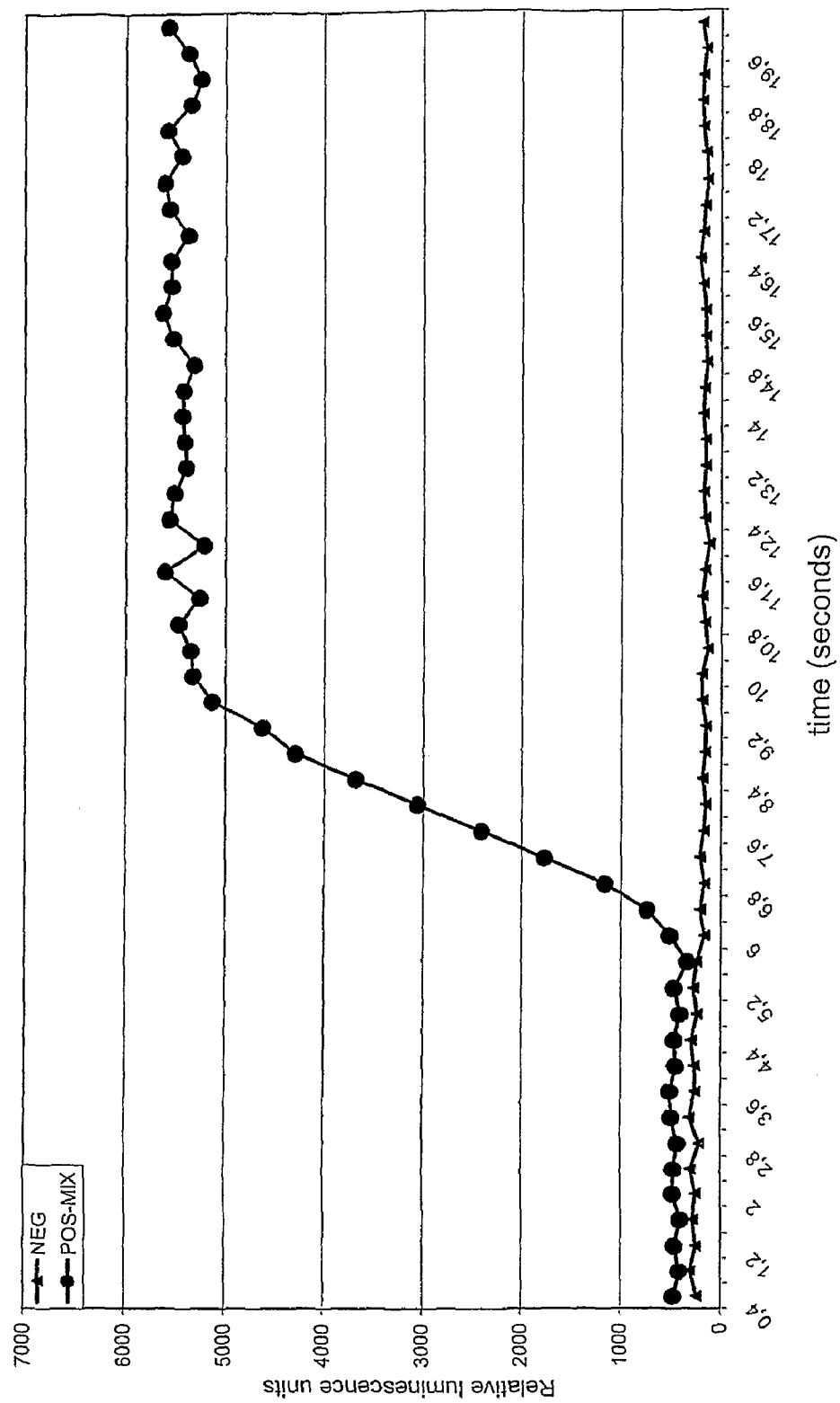

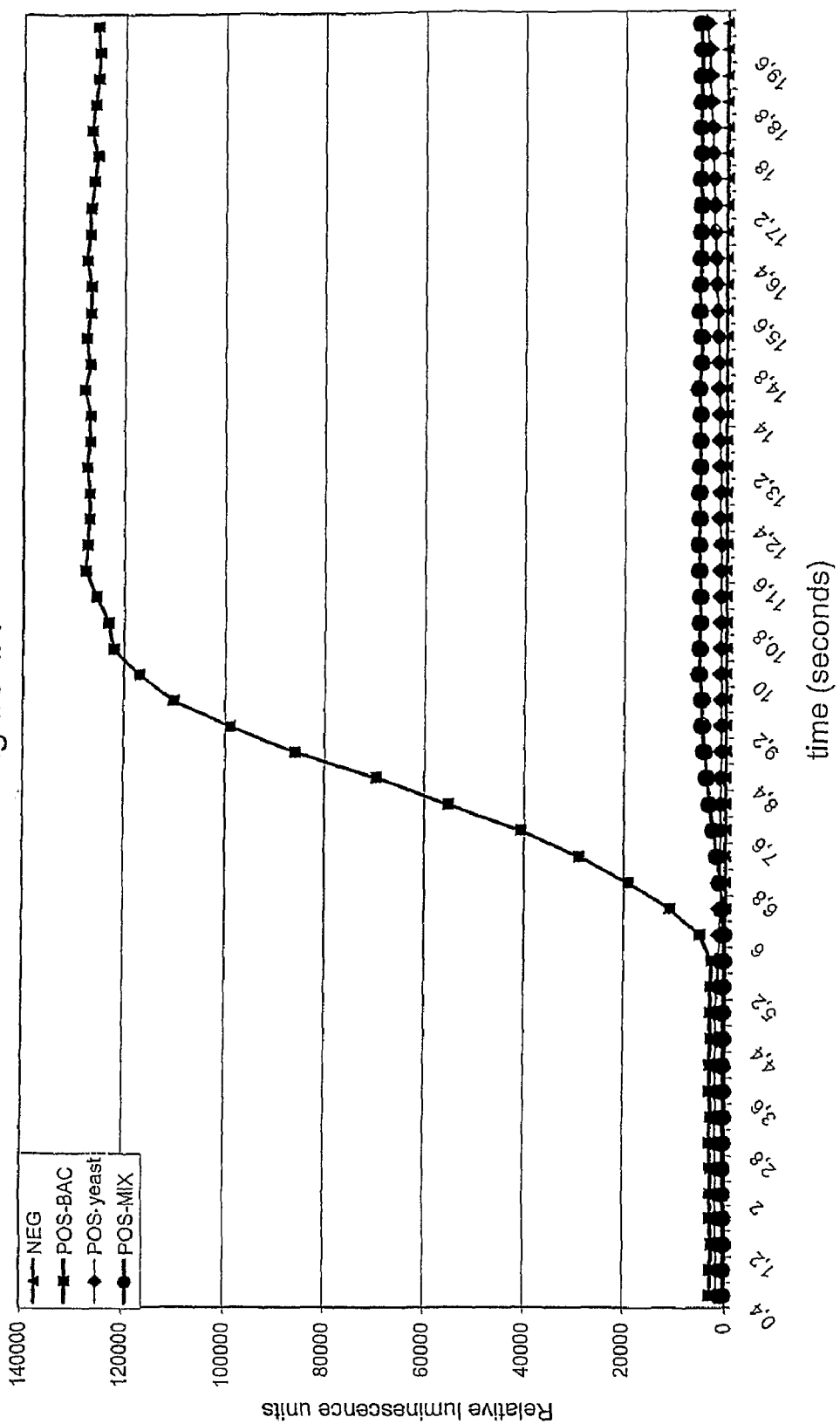

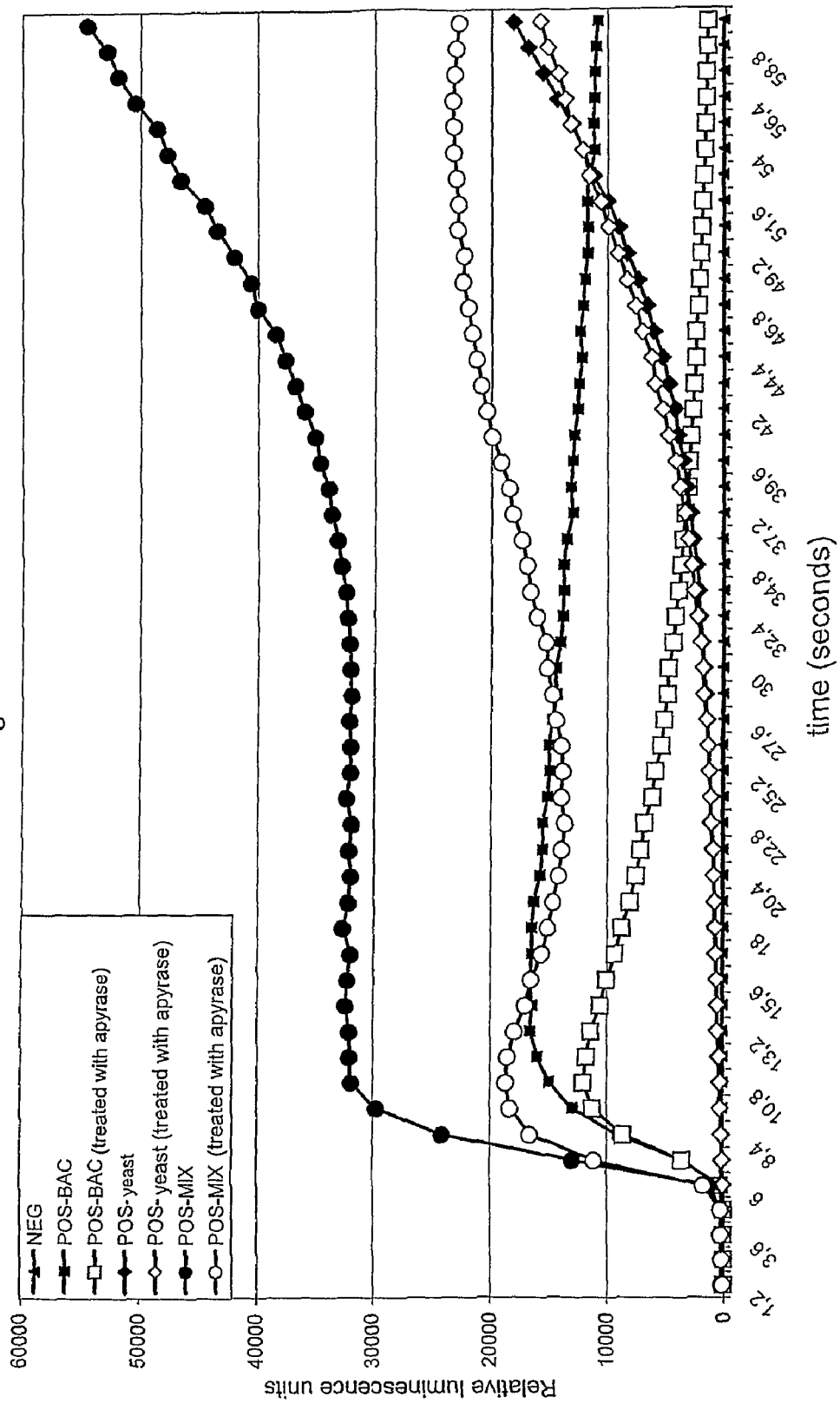

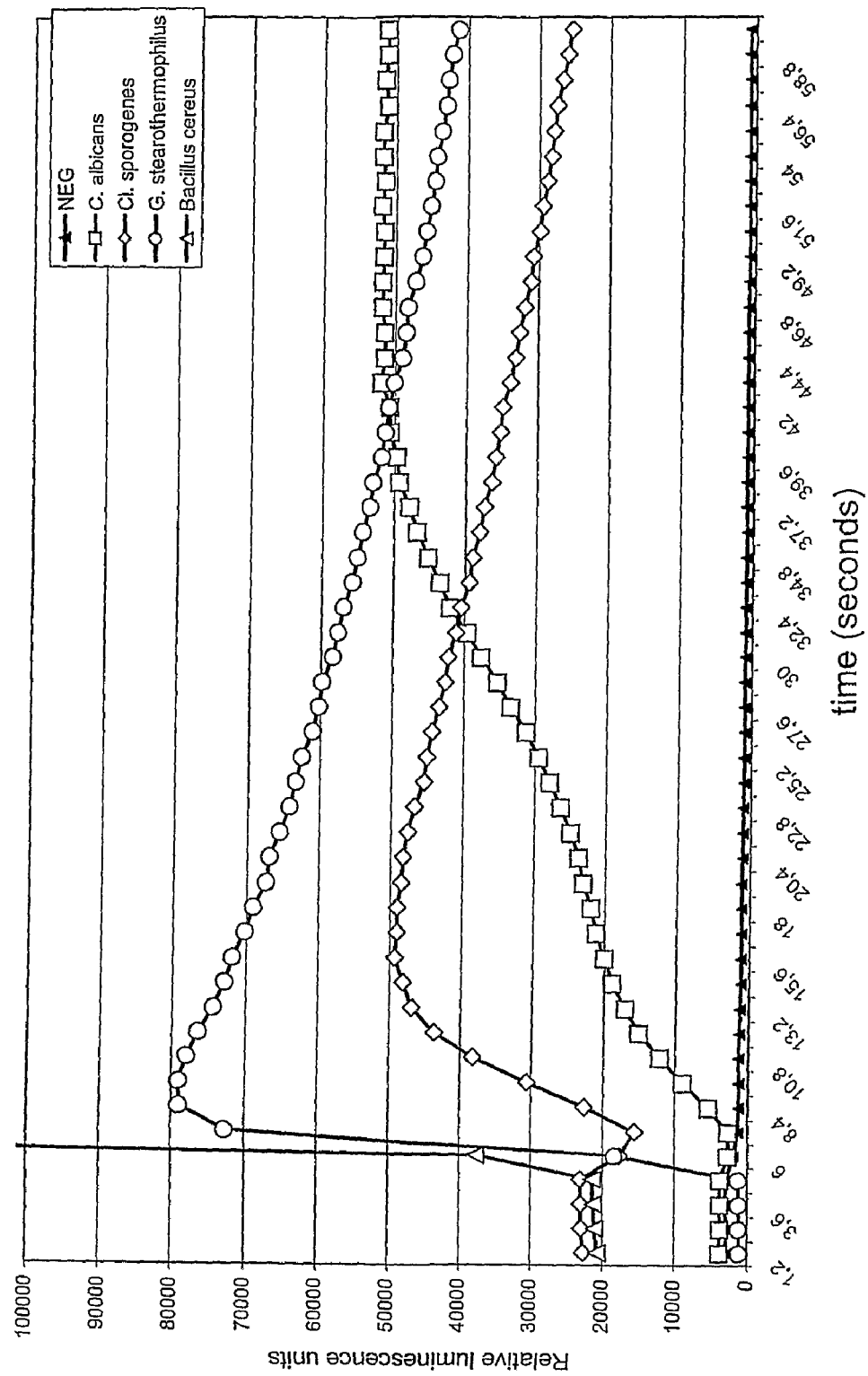

METHOD FOR DETERMINING TYPES OF CELLS

This application is a National Stage Application filed under Rule 371 based upon PCT/NL2006/000590 filed Nov. 23, 2006.

The present application relates to a method for the detection of ATP in a sample with the aid of luminescence and a computer programme for that purpose.

Several government regulations relating to the presence of contaminants hold for various industries, such as the food and beverages industry and the clinical, pharmaceutical and cosmetics industries. This for example includes an obligation to test (or arrange for the testing of) all products for the presence of contaminants such as microbial cells (for example bacteria, yeasts and fungi). Under certain conditions the presence of such microbial cells in products may cause early decay of the products. These microbial cells may moreover constitute a significant risk to the health of the consumers who consume the product.

Conventional methods for detecting microbial contamination involve the growth of microbial cells until they can be discerned with the naked eye. The disadvantage of this is that such processes are slow and it may take many days for results to be obtained. This time-consuming aspect makes such processes costly.

It has therefore been known for some time, for example from U.S. Pat. No. 4,303,752, to use a method for detecting microbial contamination in products that is based on measuring the molecule adenosine triphosphate (ATP), which is present in live microbial cells. ATP can be detected within a time span of several seconds in the presence of a luminescence reagent that for example consists of a combination of the enzyme luciferase and its cofactor luciferin. The resulting reaction, which is commonly referred to as the "firefly reaction", immediately produces a light emission known as ATP luminescence. The produced light is proportionate to the amount of ATP contained in the sample. Luminescence can be measured with the aid of a measuring instrument, such as a luminometer, for example.

From CH 678 065 it is known to defect ATP by first adding a somatic extractant, resulting in the release of somatic ATP, and subsequently a luminescence reagent. As a result, the combined amount of free ATP and somatic ATP is measured. Said combined ATP can then be removed through hydrolysis. Following that, a microbial extractant may be added so as to cause the release of microbial ATP, which ATP is subsequently measured.

From Schram et al. in Journal of Bioluminescence and Chemiluminescence, part 4, pp 390-398, 1989 there is known an improvement of the method described in CH 678 065, method employs mammal ATP-ase.

From U.S. Pat. No. 6,951,723 it is known to measure ADP (adenosine diphosphate), a decomposition product of ATP, or to convert ADP into ATP and subsequently measure it.

Significant problems may however occur when such conventional methods for ATP luminescence are used for detecting the presence of live microbial cells in products.

In the first place, ATP occurs not only in live microbial cells, but also in other non-microbial cells, which are referred to as somatic cells. Such somatic cells often form an integral part of the product. Food products and beverages may for example contain vegetable cells, for example fruit cells in fruit juices, which contain significant amounts of ATP commonly referred to as somatic ATP.

A product may also contain so-termed free ATP, which is ATP that occurs freely in a sample and derives from "dead" and/or ruptured and/or damaged somatic and/or microbial cells.

So there are three possible sources of ATP in a sample, notably free ATP, microbial ATP contained in microbial cells and somatic ATP contained in somatic cells, which three types of ATP are chemically identical and indistinguishable. So the free and somatic ATP will have to be removed before microbial ATP can be detected in order to determine the presence of microbial cells.

A second issue that has to be solved with respect to determining microbial ATP is that microbial ATP contained in microbial cells is not immediately available for activating the firefly reaction for producing luminescence. Microbial ATP contained in microbial cells must to this end first be released or extracted from the microbial cell, because the firefly reaction will only work if ATP is freely available in the sample to form a complex with the luminescence reagent (the so-termed "ATP complex"). This release is usually effected by so-termed extractants, for example quarternary ammonium compounds which as it were "puncture" a cell membrane and/or cell wall of the somatic and/or microbial cells so that ATP can flow from them. Somatic cells are more vulnerable to such extractants than microbial cells, and therefore the somatic ATP contained in somatic cells will be released first, before microbial ATP will be released from microbial cells. The release of this somatic ATP will consequently conceal the light emission of the relevant microbial ATP or lead to falsely positive results.

The above problems have been solved in the prior art first of all by using a less powerful extractant that is only suitable for releasing somatic ATP from somatic cells without rupturing the microbial cells. This results in a sample that contains free ATP and released somatic ATP in which microbial ATP is contained only in unruptured, live microbial cells. After this somatic ATP has been released, both the released somatic ATP and the free ATP already present must be eliminated before the microbial ATP can be released from microbial cells and be measured. The released somatic ATP and free ATP are eliminated by treating the sample with an enzyme commonly referred to as ATP-ase, an example of this is apyrase. Apyrase is capable of selectively decomposing free ATP contained in a sample without decomposing ATP contained in unruptured live cells such as microbial cells. This is currently the standard method used in this field.

Unruptured cells are understood to be cells whose cell wall and/or cell membrane is still intact, and which have consequently not released any ATP to their environs. Cells that are no longer "alive" will usually break down and consequently release the ATP contained in them.

The disadvantage of the aforementioned method is that apyrase remains active after free ATP and released somatic ATP have been decomposed. This means that when a microbial extractant is added and microbial ATP is released from microbial cells this will be partly decomposed by the apyrase present. Apyrase consequently has a negative influence on the measurement results, because the luminescence value obtained will be lower than expected. In particular in cases in which only a small amount of microbial cells is present this may lead to falsely negative results because all the microbial ATP will have been decomposed by apyrase before it will be possible to measure it by means of luminescence. Such a situation is undesirable because the imperceptible presence of microbial cells may lead to health risks to the user, decay and/or loss of flavour.

There is therefore a need for a method for measuring microbial ATP in a fast and reliable manner.

There is moreover a need for a method in which no falsely negative results are obtained.

BRIEF DESCRIPTION OF THE DRAWINGS

FIG. 2 presents the results of the blank measurement ("NEG") compared with the results of the measurement of the milt contaminated with yeast ("POS-YEAST").

FIG. 3 presents the results of the blank measurement ("NEG") compared with the results of the measurement of milk contaminated with bacteria and yeast ("POS-MIX").

FIGS. 4A and 4B show the diagrams of examples 1, 2 and 3 shown together in a diagram to illustrate the differences. FIG. 4B is an enlargement of FIG. 4A.

FIGS. 8A and 8B show the diagrams of examples 4-9 together in a single diagram to illustrate the differences. FIG. 8B is an enlargement of FIG. 8A.

FIG. 10B is an enlargement of FIG. 10A.

Figure 1:
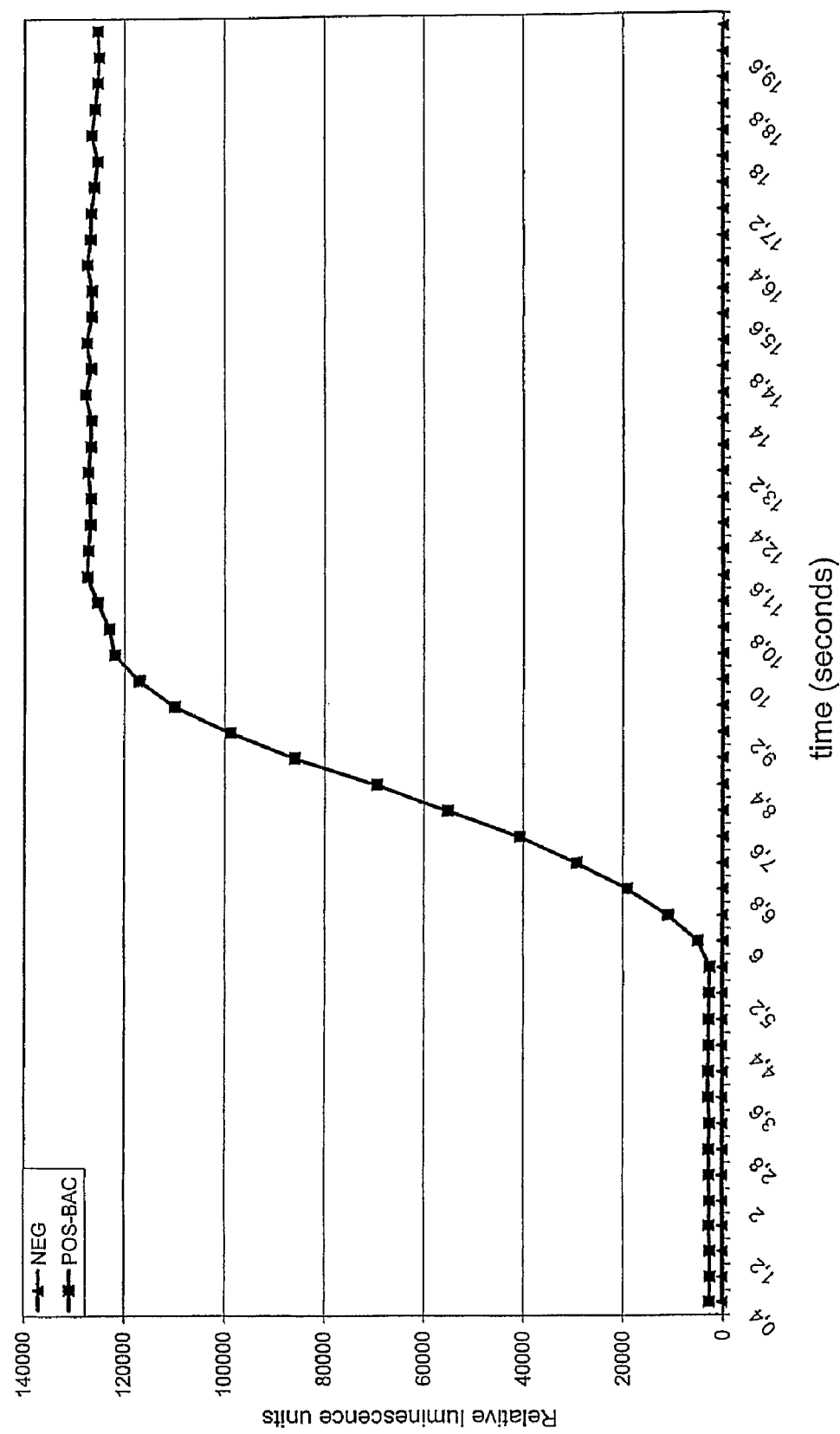
FIG. 1 presents the results of the blank measurement ("NEG") compared with the results of the measurement of the milk contaminated with bacteria ("POS-BAC").

Another aim of the present invention is to enable fast, accurate measurement of different types of microbial cells and to distinguish them from one another. There is a need for a method for distinguishing for example bacteria, yeasts and fungi from one another, and also a method for distinguishing different types of bacteria and yeasts, for example Gram-positive and Gram-negative bacteria, but also different Gram-positive bacteria from one another.

Another aim of the present invention is to determine the amount of free ATP and/or the amount of somatic ATP in a sample.

One or more of the following objectives is achieved by the method according to the introductory paragraph in which a luminescence reagent is added to a sample that has not undergone any pre-treatment with an extractant in order to effect the formation of an ATP complex, wherein the luminescence of the ATP complex thus formed in the sample is measured.

In the present invention a luminescence reagent is thus added to a sample that has not undergone any pretreatment with an extractant, for example a somatic or a microbial extractant.

It is usually preferable for the sample to be in a liquid form, that is, in suspension, emulsion or solution. Samples that are already naturally liquid may be used as such. Examples are milk, wine, fruit juice, lotions and the like. Samples that are naturally not or less liquid are prior to the measurement preferably brought into a liquid form by means of suspension, emulsion or dissolution techniques. Examples of this are vegetables, fruits, creams and the like. Samples of foodstuffs or beverages may be tested, as well as samples from other fields, such as clinical, pharmaceutical or cosmetic samples.

Use of the present method makes it possible to determine the amount of free ATP in the sample because no extractant or apyrase is added to the sample before the luminescence of the consequently unpretreated sample is measured. Such a determination of free ATP has never been carried out in the prior art.

The amount of free ATP measured according to the present method is a measure of the hygiene status of for example a factory and/or the equipment with which a particular sample has been processed, and also provides insight into any prior contaminating events of raw materials that would remain unperceived in the case of use of the method according to the state of the art. This will be explained below. The method according to the state of the art is not capable of measuring free ATP. This means that if, before being supplied to for example a factory, a contaminated sample has been heated to a certain temperature, killing the microbial cells present, this cannot be demonstrated with the method according to the state of the art. This is possible with the method according to the present invention, because free ATP is determined, which is a measure of the amount of "dead" or "damaged" ("ruptured") cells that are or were contained in the sample, from which ruptured cells ATP has been released ("free ATP"). The present invention is therefore capable of demonstrating contamination that occurred at an earlier stage. In this way it can for example be determined whether milk has been subjected to a heat treatment to kill any microbial cells before being delivered to the factory. When the method according to the state of the art is used, such milk will be classified as "not contaminated", whereas the milk will with the method according to the present invention be classified as "has been contaminated". The present method can thus be used to demonstrate that there is something "wrong" with a certain sample (on the basis of the fact that the luminescence value of the blank will be higher than a standard value), even though the product will no longer contain any intact microbial cells. An uncontaminated sample may already contain a certain amount of free ATP resulting from the product's preparation; this amount is then to be taken as the "standard", and only an increase relative to the standard value will then indicate contamination.

Another advantage of the present invention is that the use of apyrase has been (almost) completely eliminated, and the associated objections, such as falsely negative results and long waiting times, have been lessened. Use of the method of the present invention reduces the analysis time to approximately less than a minute in comparison with an analysis time of 15 to 40 minutes in the case of conventional luminescence tests of the kind described above. In special cases it may however still be preferable to use small amounts of apyrase, for example if it is expected that a large amount of somatic and free ATP will be present. Such a large amount of ATP would produce so much luminescence that the signal-noise ratio of the microbial ATP to be measured would be disturbed. In such a case apyrase may be used, but the effect of the apyrase can be simply determined and assessed via more or less continuous measurement of the luminescence throughout the analysis time, so that no falsely negative results will be obtained.

The present invention can be used to measure ATP in a multitude of products. Possible applications are in the food industry (milk and other dairy products, wine, soup, vegetable and fruit juices and products and the like), the cosmetics industry (detergents, body lotion, lipstick, sun-protection products, hair-care products and the like), the agricultural industry (freshness of cut flowers by testing sap from stems, fruits and vegetables and the like) and the clinical industry (blood samples, urine samples and other samples and the like), and the pharmaceutical industry (medicines and the like).

The method according to the present invention is preferably carried out so that the luminescence is measured for a period of at least 10 seconds. Preferably the luminescence is measured for a period of at least 20 seconds, in particular for a period of at least 60 seconds.

By measuring the luminescence with a certain regularity or continuously for a certain period of time information is obtained on such factors as the rate at which ATP is released from somatic cells in comparison with microbial cells, and between different types of somatic and microbial cells.

The luminescence is preferably measured more or less continuously to obtain the luminescence as a function of time, for example represented by a curve of the luminescence as a function of time. From the shape of this curve information can be obtained on for example the rate at which ATP is released from the various somatic and/or microbial cells, which provides information on the type of cells. This continuous measurement is also important when using apyrase, in which case a decrease in luminescence through time will be observed. It is also possible to measure the luminescence for a certain period of time with a certain interval between the individual measurements. See also the examples in which this is explained.

In a preferred embodiment the microbial cells present are identified on the basis of luminescence as a function of time through comparison with reference values as a function of time. These reference values are for example standard curves of different types of bacteria and yeasts. From such a comparison it can for example be inferred whether a particular bacterium or yeast is present, or both, and even which type of bacterium is present. This makes the present method suitable for accurately identifying different types of microbial cells, that is, for example yeasts and bacteria, for example *Candida albicans* (yeast), *Clostridium sporogenes* (Gram-positive bacterium), *Geobacillus stearothermophilus* (Gram-positive bacterium), *Bacillus cereus* (Gram-positive bacterium), *Bacillus subtilis* (Gram-positive bacterium) and *Escherichia coli* (Gram-negative bacterium).

The advantage of such an identification method is that the presence of harmful microbial cells can be distinguished from the presence of favourable or even necessary microbial cells. An example of this is the distinction between an undesired, decay-causing bacterium and yeast that is necessary for fermentation, which may both be present in pressed grapes during the process of wine-making. The method according to the state of the art can only reveal the presence of microbial cells, but cannot distinguish between the bacterium and the yeast. The present invention hence provides a solution by making it possible to make such a distinction. In certain wine-making processes the wine is moreover bottled very soon after the pressing. In such cases it is not only necessary for the right yeast to be present, but that yeast must also be removed to an adequate extent before the bottling process to prevent after-fermentation in the bottle, as that would lead to the formation of gases in the bottle, and hence to explosion of the bottle, which could be disadvantageous or even dangerous. The present invention can therefore also be used during wine-making processes to demonstrate the presence of different bacteria and fungi in different stages.

With the present invention it is possible to work with a number of standard luminescence values that can be determined for different types of products, for example standard values of non-contaminated samples, for example by measuring sterilised samples, but also standard values of samples containing for example somatic cells. These standard values may be determined prior to the method according to the present invention, or they may be provided along with the present computer program. It is for example preferable to determine three standard values for a non-contaminated sample (blank value or negative value), notably a first standard value that is a calculated average value of the measured value of a comparable, but sterilised product in the time span of 0-5 seconds, a second standard value in the time span of 5-10 seconds and a third standard value in the time span of 15-20 seconds. It will however be clear that these time spans and the number of standard values can be determined by a person skilled in the art depending on the product to be analysed and the expected contamination.

In a preferred embodiment of the present method a somatic extractant is added to the same sample after the addition of the luminescence reagent in order to effect the formation of an ATP complex, wherein the luminescence of the ATP complex thus formed in the sample is measured. In this embodiment it is hence preferable to add an excess amount of luminescence reagent relative to the free ATP present, so that sufficient uncomplexed luminescence reagent will remain for the complexing of released somatic ATP.

The ATP complex formed here is hence a complex between the luminescence reagent that was already present in the sample with the ATP released from somatic cells. In this way the amount of somatic ATP in the sample can thus be determined by means of luminescence. This ATP complex is thus added to the previously formed ATP complex between the luminescence reagent and free ATP, as described above.

Such a preferred embodiment of the present method need be carried out only if somatic cells are (may be) present in the product, which may for example be expected in beverages containing fruit juices, but to a lesser extent in cosmetic products.

With this embodiment the amount of free ATP in a sample is first measured following the addition of luminescence reagent, after which a somatic extractant is subsequently added to the same sample, preferably during the measurement of the luminescence, by means of for example an injection pump connected to the employed luminometer. The somatic extractant will damage and/or rupture the cell wall and/or membrane of somatic cells, causing somatic ATP to be released from the somatic cells, as a result of which the amount of released somatic ATP will be complexed and subsequently measured via luminescence.

In yet another preferred embodiment of the present method a microbial extractant is added to the sample thus treated with somatic extractant in order to release microbial ATP. This released microbial ATP will complex with luminescence reagent, wherein the luminescence of the ATP complex thus formed in the sample is measured.

In this embodiment ATP is first released from any somatic cells and measured, wherein ATP is released from any microbial cells that are present and is measured.

In another preferred embodiment of the present method a microbial extractant is added to the sample after the addition of the luminescence reagent for the purpose of releasing microbial ATP. The released microbial ATP will form an ATP complex with the luminescence reagent, wherein the luminescence of the ATP complex thus formed in the sample is measured.

After the amount of free ATP in the product has been determined as described above, a microbial extractant may be immediately used in order to damage and/or rupture the microbial cells in the sample. This causes the release of the microbial ATP, which can be subsequently measured in the form of an ATP complex by using luminescence. This way the presence of any microbial ATP can be determined.

The present invention further relates to a method wherein the luminesce as a function of time, measured on the sample, is compared with one or more reference values for the luminescence as a function of time for at least one cell selected from somatic cells and microbial cells, wherein it is determined whether the measured luminescence as a function of time corresponds to the reference value, in which case it is determined that the cell having said reference value is present in the sample.

The present invention also relates to a computer programme for carrying out a method for detecting ATP in a sample, in which a luminescence reagent is added to the sample that has not undergone any pre-treatment with an extractant in order to effect the formation of an ATP complex, the luminescence of the ATP complex thus formed in the sample being measured by using a luminometer in order to obtain a measured value for the luminescence of free ATP, which measured value of free ATP is compared with a standard value, wherein it is determined that ATP is present in a higher concentration if the measured value of free ATP is higher than the standard value. "In a higher concentration" is understood to be an amount of ATP that is greater than that already present in a so-termed non-contaminated blank sample. When ATP is thus present in a higher concentration this implies the presence of somatic and/or microbial cells.

The standard value is the luminescence value of a blank, non-contaminated sample. This standard value can be determined as already indicated above. If a measured value of free ATP is obtained that is more or less the same as the standard value, the sample does not contain a higher concentration of free ATP. In such a case the sample will be evaluated as "not contaminated with free ATP". If a measured value of free ATP is obtained that is higher than the standard value, the sample will be evaluated as "possibly (been) contaminated".

In a preferred embodiment of the computer programme a somatic extractant is added to the sample after the addition of the luminescence reagent in order to effect the formation of an ATP complex, the luminescence of the ATP complex thus formed in the sample being measured with the aid of a luminometer in order to obtain a measured value for the luminescence of somatic ATP, which measured value of somatic ATP is compared with the measured value obtained for free ATP as described above, wherein it is determined that somatic ATP is present if the measured value of somatic ATP is higher than the measured value of free ATP.

If a measured value of somatic ATP is obtained that is more or less the same as the value of free ATP, the sample contains no somatic ATP. In such a case the sample will be evaluated as "not contaminated with somatic cells". If a measured value of somatic ATP is obtained that is higher than the measured value of free ATP, the sample will be evaluated as "contaminated with somatic cells". This need not be a problem, as somatic cells are in some cases essential, for example in fruit juice.

In a further embodiment of the computer programme a microbial extractant is added to the sample after the addition of the somatic extractant in order to effect the formation of an ATP complex, the luminescence of the ATP complex thus formed in the sample being measured with the aid of a luminometer in order to obtain a measured value for the luminescence of microbial ATP, which measured value of microbial ATP is compared with the measured value of somatic ATP, wherein it is determined that microbial ATP is present if the measured value of microbial ATP is higher than the measured value of somatic ATP.

In yet another embodiment of the computer programme a microbial extractant is added to the sample after the addition of the luminescence reagent in order to effect the formation of an ATP complex, the luminescence of the ATP complex thus formed in the sample being measured with the aid of a luminometer in order to obtain a measured value for the luminescence of microbial ATP, which measured value of microbial ATP is compared with the measured value of free ATP as described above, wherein it is determined that microbial ATP is present if the measured value of microbial ATP is higher than the measured value of free ATP.

If a measured value of microbial ATP is obtained that is more or less the same as the measured value of free ATP and/or somatic ATP, depending on the employed method, no microbial ATP is present in the sample. In such a case the sample will be evaluated as "not contaminated with microbial cells". If a measured value of microbial ATP is obtained that is higher than the measured value of either free ATP or somatic ATP, depending on the employed method, the sample will be evaluated as "contaminated with microbial cells". This need not be a problem, as microbial cells are essential in some cases, for example yeasts in wine. In such a case it can be determined what types and species of microbial cells are present by using a number of standard curves for luminescence measurements of different types of bacteria and yeasts, as explained below.

In yet another embodiment of the present computer programme the luminescence is measured more or less continuously for a period of at least 10 seconds, preferably at least 20 and in particular at least 60 seconds, in order to obtain the luminescence as a function of time, which measurement data are compared with reference values as a function of time, for example one or more standard curves for different types of microbial and optionally somatic cells (such as certain types of bacteria, yeasts and the like), wherein it is determined which types of microbial and optionally somatic cells are contained in the sample.

EXAMPLES

The present application will be further elucidated below with reference to a number of non-restricting examples. These examples are intended to elucidate the present invention. In each example 1-11 a milk that has been inoculated with certain types of microbial cells, such as bacteria, yeasts or mixtures thereof, is used as the sample. The contaminated milk is then subjected to the method according to the present invention. The results of the luminescence measurements are shown in the figures. By using the method according to the present invention it is shown to what extent the milk is contaminated. In this way a milk sample containing unknown contaminants can be analysed for the possible presence of microbial contamination. Further samples are tested in Examples 12-13.

Employed Materials

In the test of Examples 1-11 whole milk is used as the substrate, notably UHT milk with a fat content of 3.5%. In the test of Example 12 a cosmetic sample is tested, viz. a hand lotion. In the test of Example 13 a pharmaceutical sample is tested, viz. a solution of acetylsalicylic acid (aspirin) in water. A so-termed firefly-luciferin-luciferase reagent with a stable light emission (suitable for ATP luminescence) is used as the luminescence reagent. The reagent is contained in a tris-EDTA buffer with a pH of 7.75. Apyrase obtained from potato contained in a tris-EDTA buffer with a pH of 7.75 is used as the apyrase reagent. A mixture of quaternary ammonium compounds and surfactants in water is used as the microbial extractant. A mixture of detergents in water is used as the somatic extractant.

A computer-controlled luminometer with a low-noise photomultiplier for counting individual photons is used as the luminometer (PromiLite III from Promicol). Injector pumps control the supply of reagents to the sample. The sample is introduced into a 96-well microtitre plate, each sample being introduced into a separate well.

In each of the Examples 1-11 a blank sample, referred to as "NEG" or negative in the diagrams, is used in each test. This means that this sample contains no microbial ATP, since it is a non-inoculated sterile milk, and is hence free of microbial contamination. This blank is obtained by incubating an unopened carton of milk (1-liter paper carton) at 32° C. for 24 hours. In addition to the blank, one or more contaminated samples, which have been inoculated with one or more types of bacterium, yeast and/or mixtures thereof, are used in each example. They are in the diagrams referred to as "POS-BAC", "POS-YEAST" and "POS-MIX", respectively. The diagrams show the relative luminescence unit as a function of time in seconds. The measurements are in the examples carried out for 20 or 60 seconds. The measurements of Examples 12-13 are not shown in the diagrams.

Example 1

Preparation of "POS-BAC": a culture of the bacterium *Bacillus subtilis* was prepared in a resuscitation medium and incubated at 32° C. for 24 hours. Next, 50 µl of the culture was added to 20 ml of milk and incubated at 32° C. for 24 hours. Such a sample is to be regarded as a sample that has not been pretreated with an extractant.

Measurement: 50 µl of "NEG" milk and 50 µl of "POS-BAC" milk were pipetted into a microtitre plate and subjected to luminescence measurement according to the following process sequence:
  Connection of holder with luminescence reagent to injector pump 1
  Connection of holder with microbial extractant to injector pump 2
  Injection of 50 µl of luminescence reagent
  Delay of 2.05 seconds
  Start of measurement at time t=0 with a measuring interval of 0.4 second
  Injection of 50 µl of microbial extractant into all the wells at time t=5 seconds
  End of measurement at time t=20 seconds.

The results obtained are shown in FIG. 1, in which the diagram presenting the results of the blank measurement ("NEG") is compared with the results of the measurement of the milk contaminated with bacteria ("POS-BAC").

It can be inferred from FIG. 1 that in the time interval from t=0 to t=5 the value of "POS-BAC" is a little higher than the value of "NEG", which means that the milk contaminated with bacteria contains a certain amount of free ATP, implying the presence of bacterial cells that have already died, which may hence serve as a kind of warning of possible contamination of the milk. The microbial extractant that will rupture the microbial cells present and will cause the release of the microbial ATP present is added at time t=5. It can be inferred from the diagram that some of the microbial cells have released their ATP after 1 second (time t=6) already. This process of the release of microbial ATP lasts approximately until time t=10. After this the luminescence remains constant, showing that all the microbial ATP has been released.

It can be clearly inferred from FIG. 1 that the method according to the present invention can be used to determine the presence of bacterial contamination in milk.

Example 2

Preparation of "POS-YEAST": a culture of a wild yeast strain that frequently occurs as natural contamination of fruit juices was prepared in a resuscitation medium and incubated at 26° C. for 24 hours. Next, 50 µl of the culture was added to 20 ml of milk and this was again incubated at 26° C. for 24 hours. Such a sample is to be regarded as a sample not pretreated with an extractant. This example differs from example 1 in that yeast was used instead of bacteria.

Measurement: 50 µl of "NEG" milk and 50 µl of "POS-YEAST" milk were pipetted into a microtitre plate and subjected to luminescence measurement according to the same process sequence as described in example 1.

The results obtained are shown in FIG. 2, in which the diagram presenting the results of the blank measurement ("NEG") is compared with the results of the measurement of the milk contaminated with yeast ("POS-YEAST").

It can be inferred from FIG. 2 that the value of "POS-YEAST" is in the time interval from t=0 to t=5 a little higher than the value of "NEG", which means that the milk contaminated with yeast contains a certain amount of free ATP, implying the presence of yeast cells that have already died, which may hence serve as a kind of warning of possible contamination of the milk. The microbial extractant that will rupture the microbial cells present and will cause the microbial ATP present to be released is added at time t=5. It can be inferred from the diagram that a decrease in the luminescence occurs immediately after the addition of the microbial extractant. This decrease is attributable to two factors, the first being a dilution effect following the addition of the microbial extractant and the second being a so-termed quenching effect. It is also visible that some of the microbial cells have released their ATP only after approximately 5 seconds (time t=10), which is slower than in the case of bacteria (see example 1). This process of the release of microbial ATP lasts until the end of the analysis (t=20).

It can be clearly inferred from FIG. 2 that the method according to the present invention can be used for determining the presence of contamination by yeast in milk.

Example 3

Preparation of "POS-MIX": a mixture of "POS-BAC" milk, prepared according to example 1, and "POS-YEAST" milk according to example 2 is prepared so that the estimated amounts of micr. ATP of both types of microbial contaminants are in the same order of magnitude (bacteria:yeast=1:30). Such a sample is to be regarded as a sample that has not been pretreated with an extractant. Example 3 differs from examples 1 and 2 in that a combination of bacteria and yeast is used.

Measurement: 50 µl of "NEG" milk and 50 µl of "POS-MIX" milk were pipetted into a microtitre plate and subjected to luminescence measurement according to the same process sequence as described in example 1.

The results obtained are shown in FIG. 3, in which the diagram presenting the results of the blank measurement ("NEG") is compared with the results of the measurement of milk contaminated with bacteria and yeast ("POS-MIX").

It can be inferred from FIG. 3 that the value of "POS-MIX" is in the time interval from t=0 to t=5 slightly higher than the value of "NEG", which means that the milk contaminated with bacteria and yeast contains a certain amount of free ATP, implying the presence of microbial cells that have already died, which may hence serve as a kind of warning of possible contamination of the milk. The microbial extractant that will rupture the microbial cells present and will cause the microbial ATP present to be released is added at time t=5. It can be inferred from the diagram that a decrease in luminescence occurs immediately after the addition of the microbial extractant, as described in example 2. Some of the microbial cells have released their ATP after approximately 1 second (time t=6) already. This process of the release of microbial ATP lasts until time t=10.

It can be clearly inferred from FIG. 3 that the method according to the present invention can be used to determine the presence of contamination by both bacteria and yeast in milk.

Figure 4B:
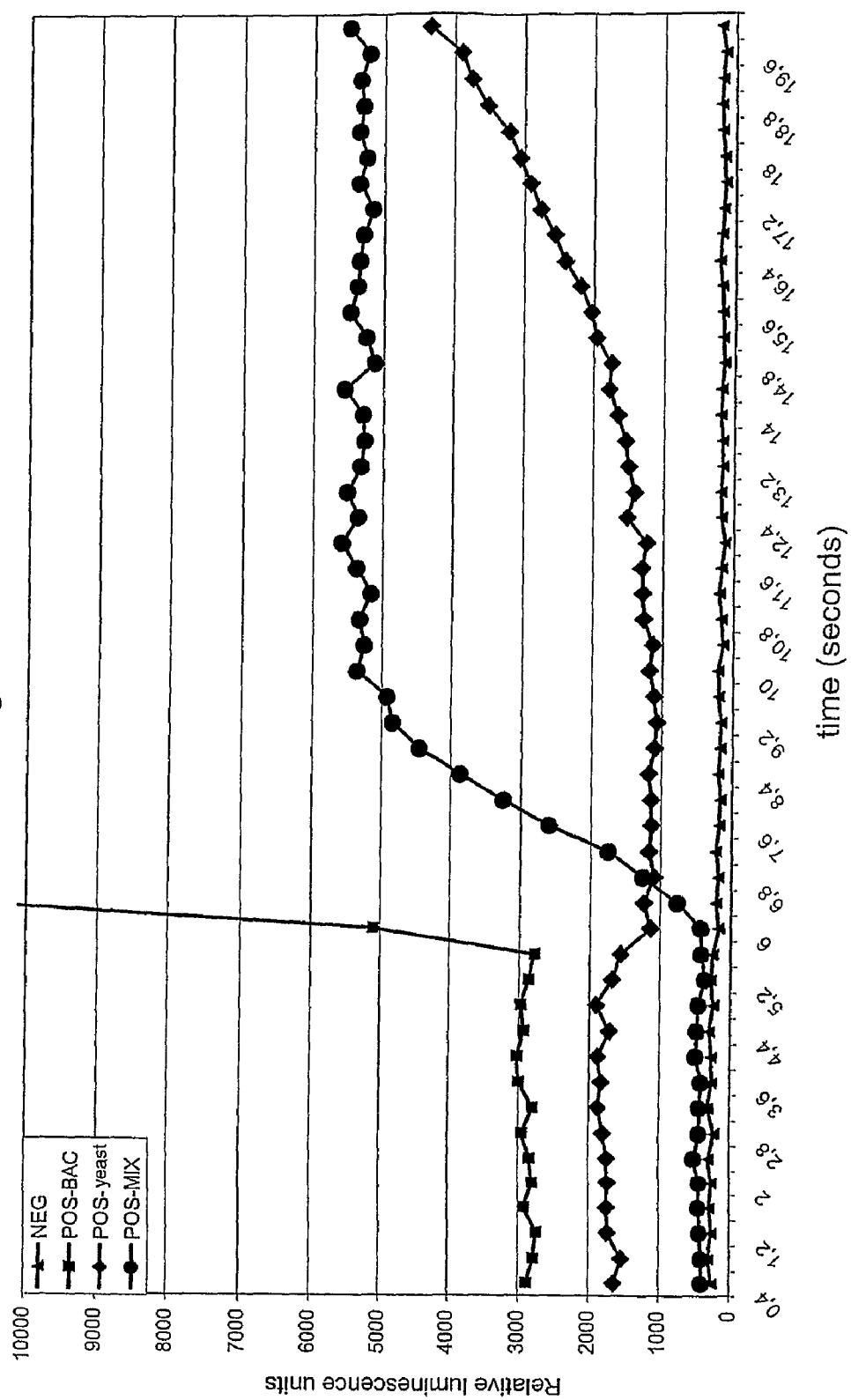

In FIGS. 4A and 4B the diagrams of examples 1, 2 and 3 are shown together in a diagram to illustrate the differences. FIG. 4B is an enlargement of FIG. 4A. This shows that there is a substantial difference between the results of milk contaminated with bacteria and with yeast. The milk contaminated with bacteria shows a luminescence profile characterised by a rapid increased in luminescence after the addition of microbial extractant, the rapid establishment of a constant luminescence value and also a higher luminescence value, whereas the milk contaminated with yeast shows a profile with a slow increase in luminescence after the addition of microbial extractant, without the establishment of a constant luminescence value in the time span of 20 seconds, and also with a lower luminescence value.

This comparison clearly shows that the present method is not only suitable for demonstrating the presence of microbial contamination, but also for determining what type (yeast or bacteria or a combination) is present.

Example 4

Preparation of "POS-BAC": a culture of the bacterium *Bacillus cereus* (ATCC 11778) in a resuscitation medium was prepared and incubated at 32° C. for 24 hours. Next, 50 µl of the culture was added to 20 ml of milk and again incubated at 32° C. for 24 hours. Such a sample is to be regarded as a sample that has not been pretreated with an extractant. The difference with respect to example 1 is that a different type of bacterium was used.

Measurement: 50 µl of "NEG" milk and 50 µl of "POS-BAC" milk were pipetted into a microtitre plate and subjected to luminescence measurement according to the following process sequence:
Connection of holder with luminescence reagent to injector pump 1
Connection of holder with microbial extractant to injector pump 2
Injection of 50 µl of luminescence reagent
Delay of 2.05 seconds
Start of measurement at time t=0 with a measuring interval of 1.2 seconds
Injection of 50 µl of microbial extractant into all the wells at time t=5 seconds
End of measurement at time t=60 seconds.

Figure 5:
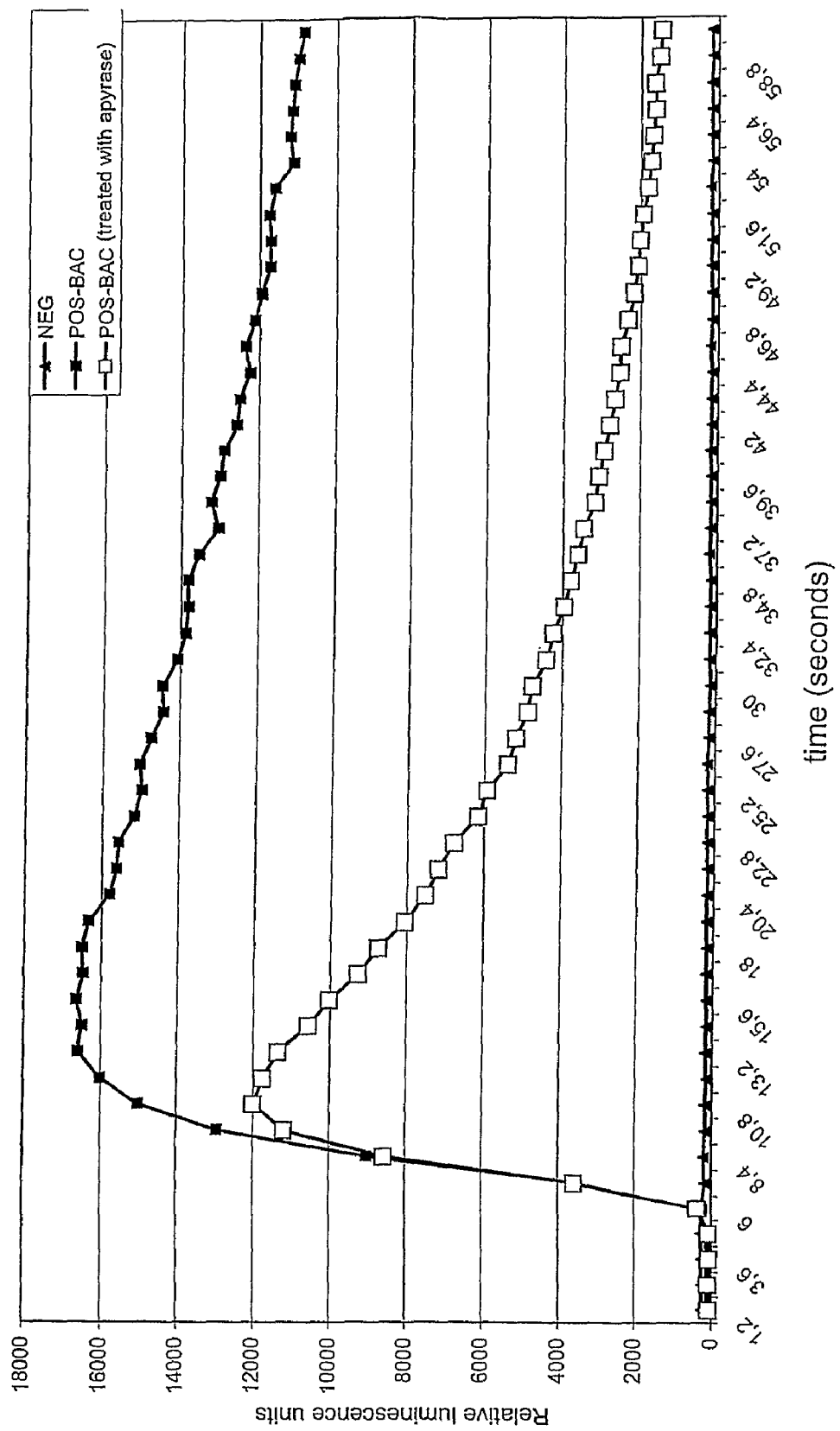
FIG. 5 presents the results of the blank measurement ("NEG") compared with the results of the measurement of the milk contaminated with bacteria ("POS-BAC").

The results obtained are shown in FIG. 5, in which the diagram presenting the results of the blank measurement ("NEG") is compared with the results of the measurement of the milk contaminated with bacteria ("POS-BAC").

Example 5

Preparation of "POS-BAC (treated with apyrase)": a "POS-BAC" milk as described in example 4 was prepared.

Measurement: 50 µl of "NEG" milk and 50 µl of "POS-BAC (treated with apyrase)" milk were pipetted into a microtitre plate. Amounts of 50 µl of apyrase were added to each well and incubated for 15 minutes. The samples were subsequently subjected to luminescence measurement according to the same process sequence as described in example 4.

The results obtained are shown in FIG. 5, in which the diagram presenting the results of the blank measurement ("NEG") is compared with the results of the measurement of the milk contaminated with bacteria ("POS-BAC (treated with apyrase)").

It can be inferred from the "POS-BAC" curve (example 4) in FIG. 5 that, after a rapid increase in luminescence in the time span from t=6 to t=10, the luminescence remains constant for some time (up to t=20), after which a decrease in luminescence is observed. It is not known to what this decrease is attributable, but the present inventors are of the opinion that some decomposition may take place of the complex formed between microbial ATP and the luminescence reagent.

It can be inferred from the "POS-BAC (treated with apyrase)" curve (example 5) in FIG. 5 that, after a comparable rapid increase in luminescence in the time span from t=6 to t=10, the luminescence value is lower than that of "POS-BAC". That means that the treatment with apyrase according to example 5 leads to a lower value, which is caused by the decomposition of released microbial ATP by the apyrase present. The luminescence does moreover not reach a constant value, but decreases through time more rapidly than "POS-BAC" according to example 4, which has not undergone any apyrase treatment. This hence shows that the disadvantages of apyrase can be solved in part at least by the present invention. In the present example the apyrase treatment leads to a lower luminescence, but it will be clear that in a case in which only a small amount of microbial cells is present the apyrase treatment could even lead to a "falsely" negative result.

It can hence be clearly inferred from FIG. 5 that the method according to the present invention solves the problems involved in the apyrase treatment according to the state of the art in part at least.

Example 6

Preparation of "POS-YEAST": a "POS-YEAST" milk is prepared as indicated in example 2.

Measurement: 50 µl of "NEG" milk and 50 µl of "POS-YEAST" milk were pipetted into a microtitre plate and subjected to luminescence measurement according to the same process sequence as described in example 4.

Figure 6:
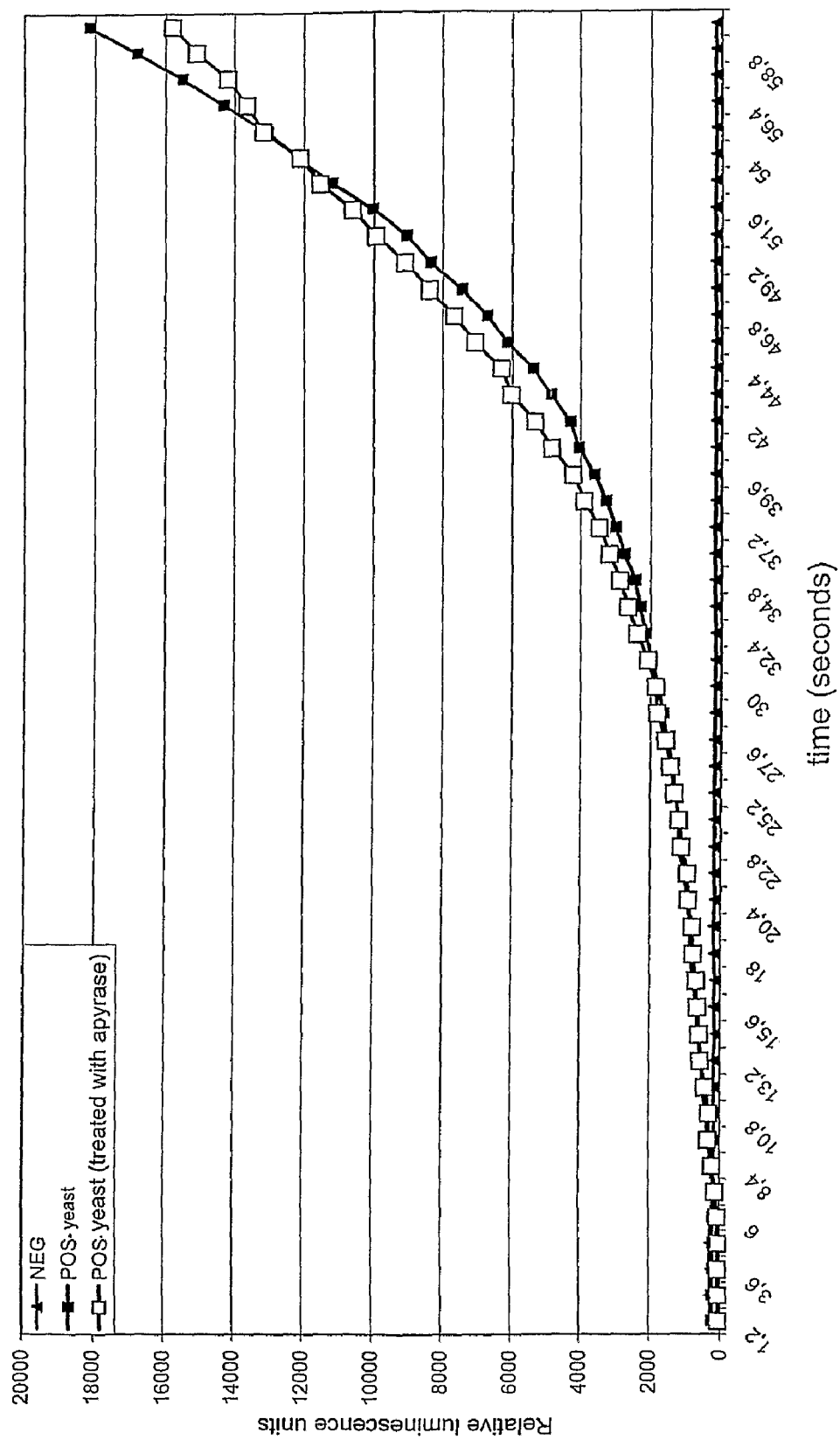
FIG. 6 presents the results of the blank measurement ("NEG") compared with the results of the measurement of the milk contaminated with yeast ("POS-YEAST").

The results obtained are shown in FIG. 6, in which the diagram presenting the results of the blank measurement ("NEG") is compared with the results of the measurement of the milk contaminated with yeast ("POS-YEAST").

Example 7

Preparation of "POS-YEAST (treated with apyrase)": a "POS-YEAST" milk as described in example 4 was prepared.

Measurement: 50 μl of "NEG" milk and 50 μl of "POS-YEAST (treated with apyrase)" milk were pipetted into a microtitre plate. Amounts of 50 μl of apyrase were added to each well and incubated for 15 minutes. The samples were subsequently subjected to luminescence measurement according to the same process sequence as described in example 4.

The results obtained are shown in FIG. 6, in which the diagram presenting the results of the blank measurement ("NEG") is compared with the results of the measurement of the milk contaminated with yeast ("POS-YEAST (treated with apyrase)").

It can be inferred from the "POS-YEAST" curve (example 6) in FIG. 6 that a slow increase in luminescence is observed, which lasts until the end of the measurement at t=60.

It can be inferred from the "POS-YEAST (treated with apyrase)" curve (example 7) in FIG. 6 that there are minor differences with respect to the "POS-YEAST" curve according to example 6. The ultimate luminescence value is slightly lower in the case of the apyrase treatment and the shape of the curve is slightly different.

Example 8

Preparation of "POS-MIX": a mixture is prepared of "POS-BAC" milk prepared according to example 4 and "POS-YEAST" milk according to example 6 so that the estimated amount of microbial ATP of both types of microbial contaminants is in the same order of magnitude (bacteria:yeast=1:10).

Measurement: 50 μl of "NEG" milk and 50 μl of "POS-MIX" milk were pipetted into a microtitre plate and subjected to luminescence measurement according to the same process sequence as described in example 4.

Figure 7:
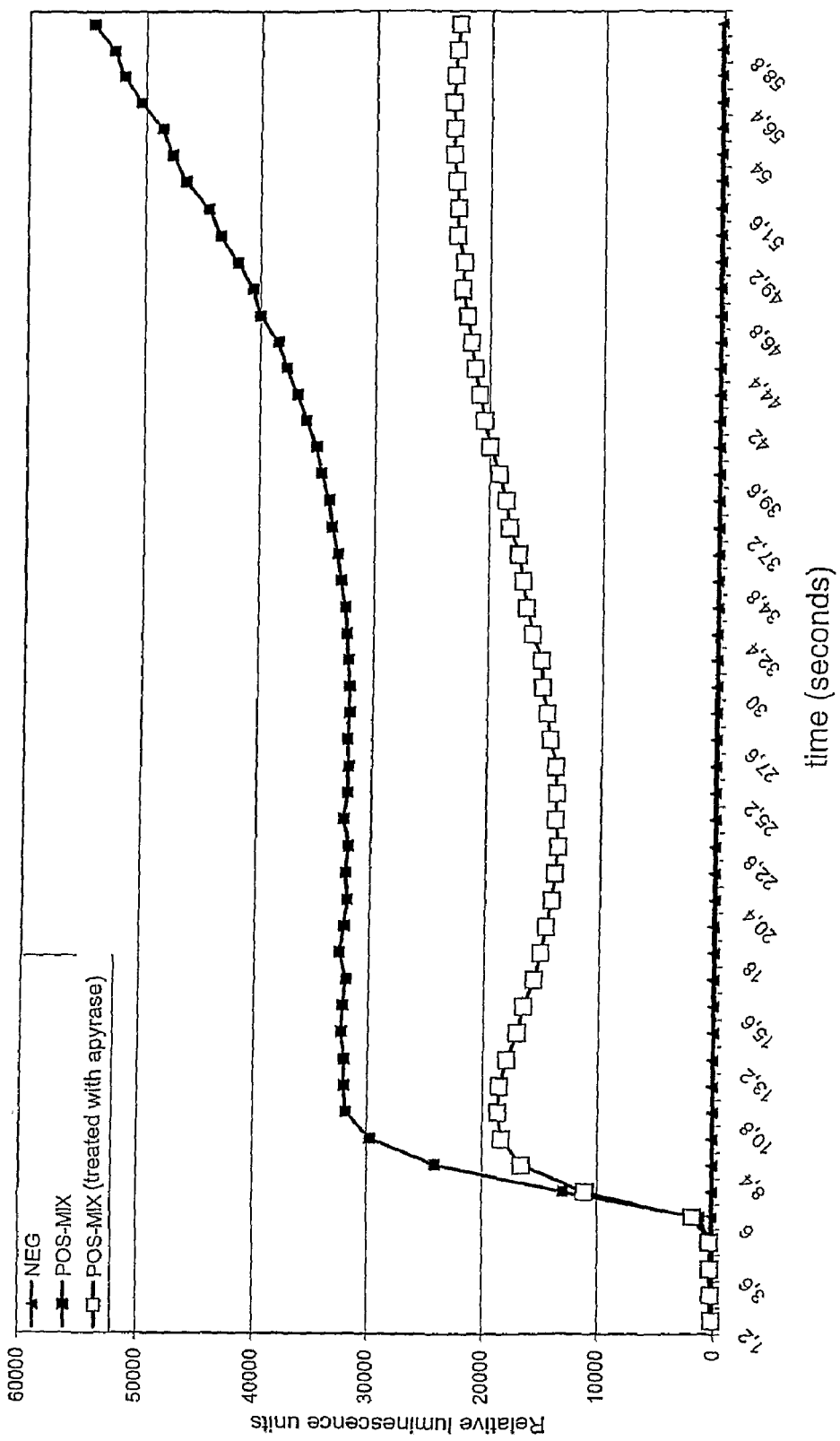
FIG. 7 presents the results of the blank measurement ("NEG") compared with the results of the measurement of the milk contaminated with bacteria and yeast ("POS-MIX").

The results obtained are shown in FIG. 7, in which the diagram presenting the results of the blank measurement ("NEG") is compared with the results of the measurement of the milk contaminated with bacteria and yeast ("POS-MIX").

Example 9

Preparation of "POS-MIX (treated with apyrase)": a "POS-MIX" milk as described in Example 6 was prepared.

Measurement: 50 μl of "NEG" milk and 50 μl of "POS-MIX (treated with apyrase)" milk were pipetted into a microtitre plate. Amounts of 50 μl of apyrase were added to each well and incubated for 15 minutes. The samples were subsequently subjected to luminescence measurement according to the same process sequence as described in example 4.

The results obtained are shown in FIG. 7, in which the diagram presenting the results of the blank measurement ("NEG") is compared with the results of the measurement of the milk contaminated with bacteria and yeast ("POS-MIX (treated with apyrase)").

It can be inferred from the "POS-MIX" curve (example 8) in FIG. 7 that, after a rapid increase in luminescence in the time interval from t=6 to t=10, the luminescence remains constant for some time (up to t=30), after which a further increase in luminescence is observed up to t=60. This further increase is attributable to the rupturing of the yeast cells present and the release of the microbial ATP from them.

It can be inferred from the "POS-MIX (treated with apyrase)" curve (example 9) in FIG. 7 that, after a comparably fast increase in luminescence in the time interval from t=6 to t=10, the value of the luminescence is lower than that of "POS-MIX". In addition, a decrease in luminescence is observed, followed by a slight, temporary increase. This decrease is attributable to the decomposition of some ATP present by apyrase, and the increase is attributable to the rupturing of yeast cells as described above. This increase and decrease counterbalance one another, consequently resulting in a falsely negative result for the presence of yeast in this sample, which is not obtained with the method according to example 8.

The above shows that the treatment with apyrase according to example 9 results in a lower value, caused by the decomposition of microbial released ATP by the apyrase present. This hence shows that the disadvantages of apyrase can be solved in part at least by the present invention.

Figure 8B:
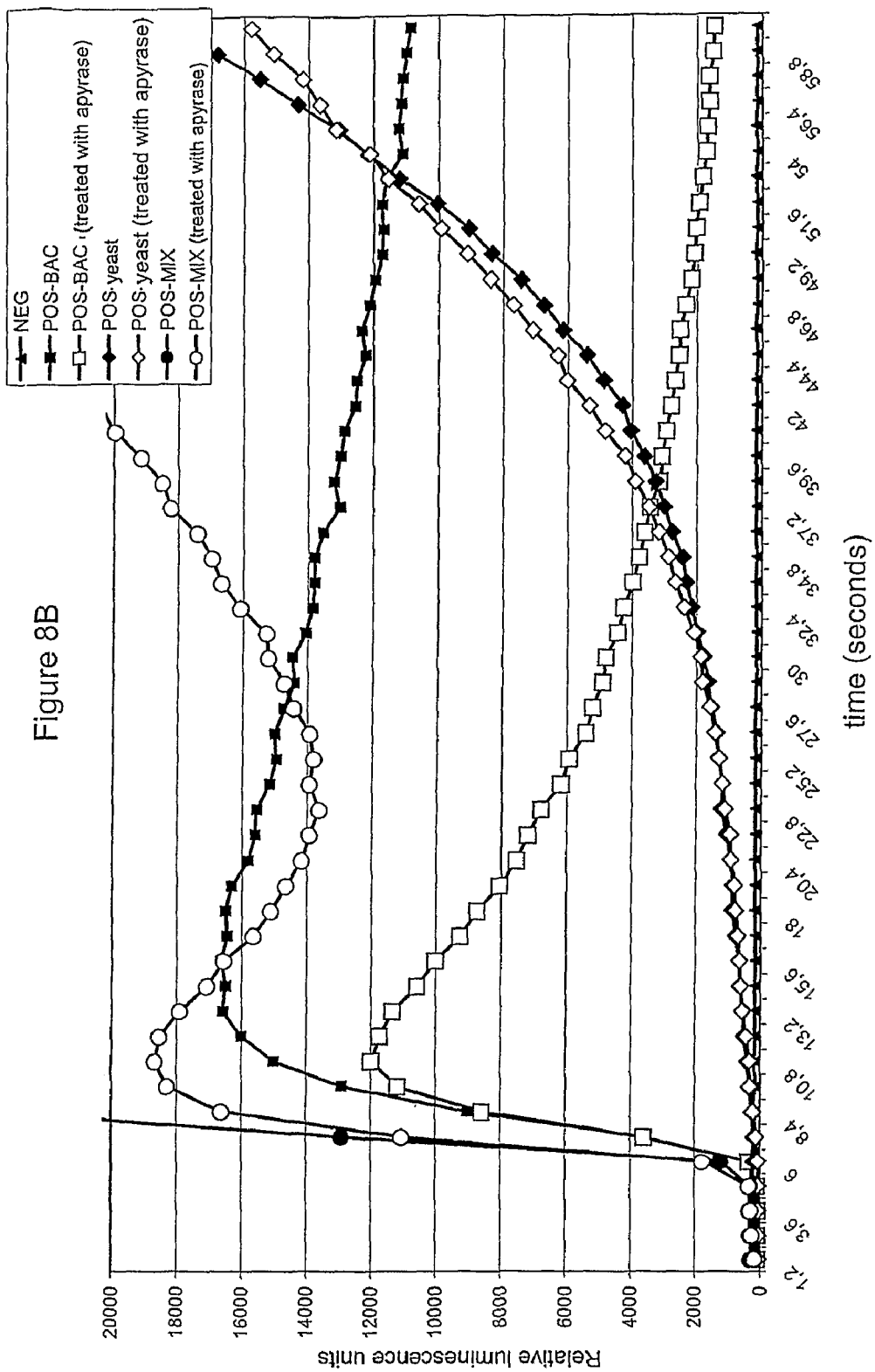

FIGS. 8A and 8B show the diagrams of examples 4-9 together in a single diagram to illustrate the differences. FIG. 8B is an enlargement of FIG. 8A, which shows that there is a substantial difference between the results of milk contaminated with bacteria and with yeast, comparable with what has been discussed above in relation to FIGS. 4A and 4B. This comparison clearly sows that the present method is suitable not only for demonstrating the presence of microbial contamination, but also for determining what type (yeast or bacteria or a combination) is present.

Example 10

Preparation of "POS-YEAST": a culture as described in example 2 is prepared. Next, 50 μl of the culture was added to 20 ml of vanilla-lemon flavoured milk and again incubated at 26° C. for 24 hours. The difference with respect to previous examples is that this sample contains somatic cells.

Measurement: 50 μl of "NEG" milk and 50 μl of "POS-YEAST" milk were pipetted into a microtitre plate and subjected to luminescence measurement according to the following process sequence:

Connection of holder with luminescence reagent to injector pump 1
Connection of holder with microbial extractant to injector pump 2
Connection of holder with somatic extractant to injector pump 3
Injection of 50 μl of luminescence reagent
Delay of 2.05 seconds
Start of measurement at time t=0 with a measuring interval of 0.56 second
Injection of 50 μl of somatic extractant into all the wells at time t=3 seconds
Injection of 50 μl of microbial extractant into all the wells at time t=8 seconds
End of measurement at time t=28 seconds.

Figure 9:
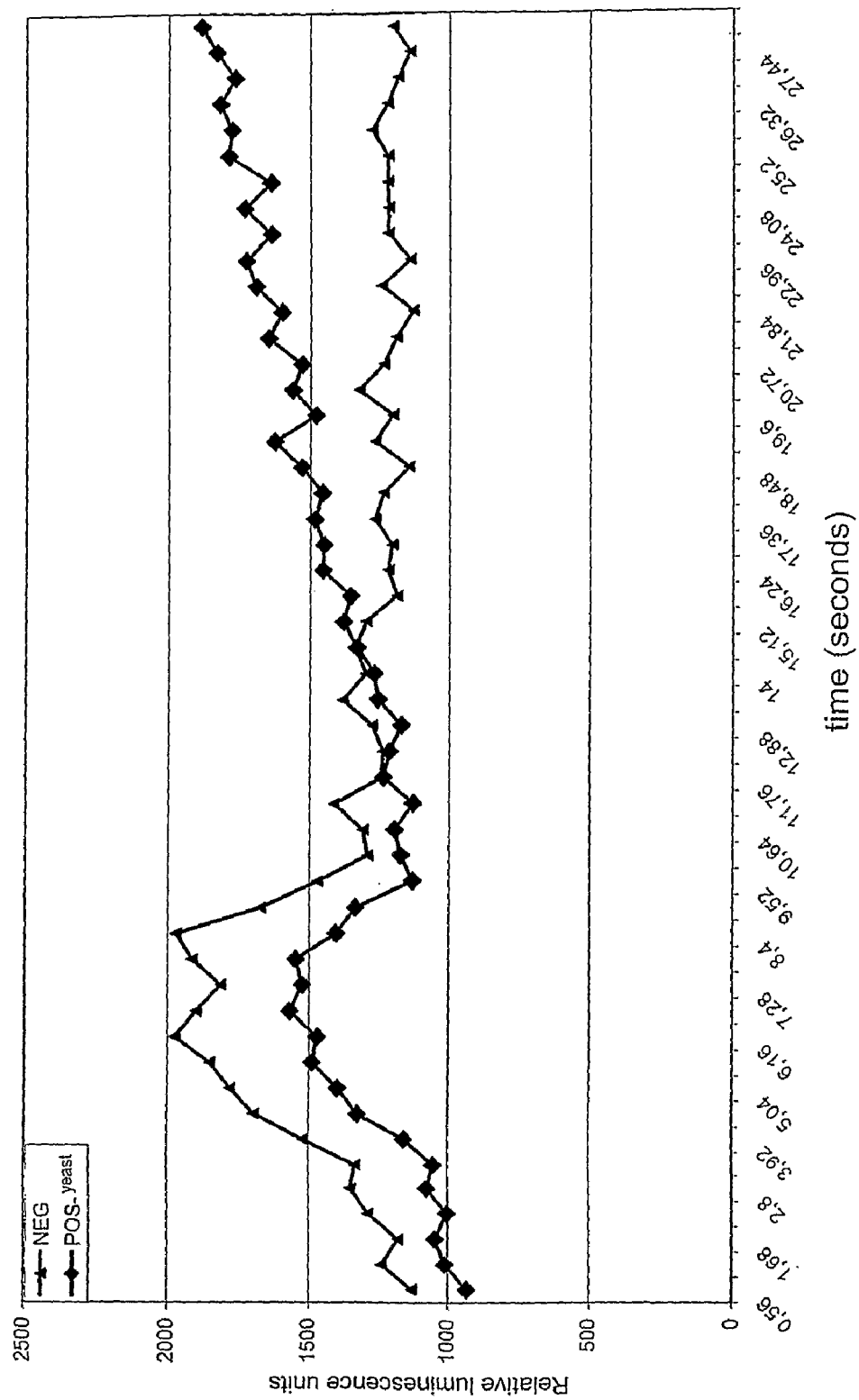
FIG. 9 presents the results of the blank measurement ("NEG") compared with the results of the measurement of the milk contaminated with yeast ("POS-YEAST").

The results obtained are shown in FIG. 9, in which the diagram presenting the results of the blank measurement ("NEG") is compared with the results of the measurement of the milk contaminated with yeast ("POS-YEAST").

It can be inferred from FIG. 9 that in the time interval from t=0 to t=5 the "POS-YEAST" value is slightly higher than the "NEG" value, which means that the milk contaminated with yeast contains a certain amount of free ATP, implying the presence of yeast cells that have already died, which can hence serve as a warning of possible contamination of the milk. It can also be seen that the "NEG" milk also contains a certain amount of ATP, which indicates the presence of free ATP, probably somatic ATP from vegetable cells (vanilla-lemon flavouring). The somatic extractant that will rupture the somatic cells present and will cause the ATP present to be released is added at time t=3. It can be inferred from the diagram that an increase in luminescence takes place immediately after the addition of the somatic extractant, in both the "NEG" milk and the "POS-YEAST" milk, implying that both samples contain somatic cells, deriving from the vanilla-lemon flavouring. The microbial extractant that will rupture the microbial cells present and will cause the ATP present to be released is added at time t=8. It can be inferred from the diagram that a decrease in luminescence occurs immediately after the addition of the microbial extractant, as already described above in example 2. This initial decrease is followed by a slow increase in luminescence in the case of the "POS-YEAST" milk, but not in the case of the "NEG" milk, which shows that the "POS-YEAST" milk contains microbial contamination and the "NEG" milk contains no microbial contamination. This process of the release of microbial ATP in the "POS-YEAST" milk lasts until the end of the analysis (t=28).

It can be clearly inferred from FIG. 9 that the method according to the present invention can be used to determine the presence of both somatic and microbial contamination in milk in a single measurement process, which has hitherto been found to be impossible with the method according to the state of the art.

Example 11

As already indicated above, the present method is extremely suitable for identifying different types of yeasts and bacteria. In this example a yeast and three Gram-positive bacteria were compared with one another in order to assess whether they can be distinguished from one another on the basis of the present method.

The employed microbial cells are *Candida albicans* (yeast; ATCC 10231), *Geobacillus stearothermophilus* (Gram-positive bacterium; ATCC 7953), *Clostridium sporogenes* (Gram-positive bacterium; ATCC 19404), *Bacillus cereus* (Gram-positive bacterium; ATCC 11778).

Preparation of "C. albicans": a colony of the yeast *Candida albicans* on a tryptic soy agar-agar plate was introduced into 9 ml of resuscitation medium and incubated at 22-25° C. for 24 hours.

Preparation of "G. stearothermophilus": a colony of the bacterium *Geobacillus stearothermophilus* on a tryptic soy agar-agar plate was introduced into 9 ml of resuscitation medium and incubated at 55° C. for 24 hours.

Preparation of "C. Sporogenes": a colony of the bacterium *Clostridium sporogenes* on a blood agar-agar plate was introduced into 9 ml of liquid thioglycolate medium and incubated at 35° C. for 24 hours.

Preparation of "B. cereus": a colony of the bacterium *Bacillus cereus* on a tryptic soy agar-agar plate was introduced into 9 ml of resuscitation medium and incubated at 35° C. for 24 hours.

Preparation of "NEG": the resuscitation medium was incubated at 35° C. for 24 hours.

Measurement: 50 µl of "NEG" and 50 µl each of "C. albicans", "G. stearothermophilus", "C. Sporogenes" and "B. cereus" were pipetted into a microtitre plate and subjected to luminescence measurement according to the process sequence described in example 4.

Figure 10:
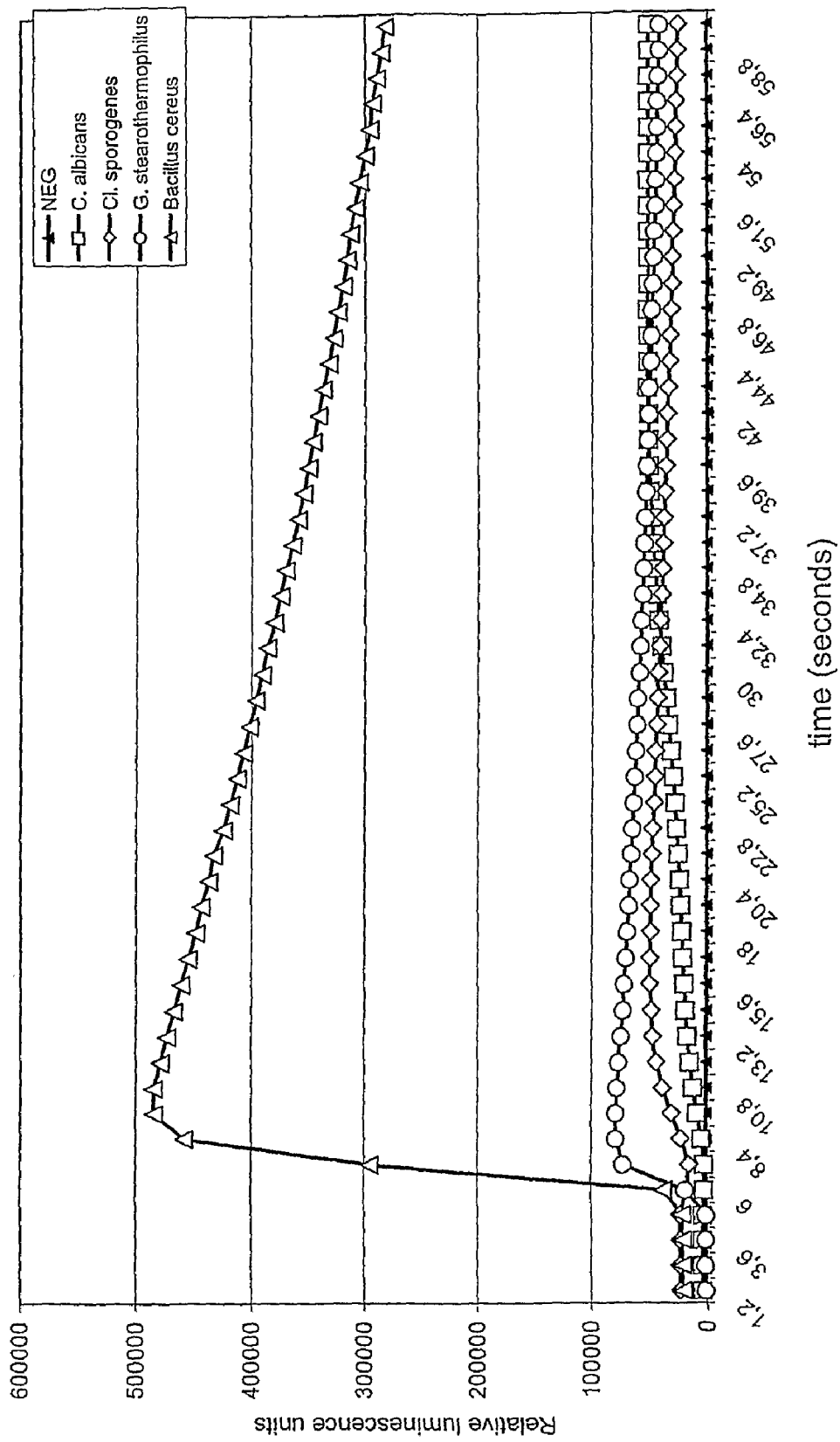
FIGS. 10A and 10B present the results of the blank measurement ("NEG") compared with the results of the measurements of the samples contaminated with various microbial cells.

The results obtained are shown in FIGS. 10A and 10B, in which the diagram presenting the results of the blank measurement ("NEG") is compared with the results of the measurement of the samples contaminated with various microbial cells. FIG. 10B is an enlargement of FIG. 10A.

It can be inferred from FIG. 10B that in the time interval from t=0 to t=5 the values of "B. cereus" and "Cl. sporogenes" are slightly higher than the value of "NEG", which means that the samples contaminated with bacteria contain a certain amount of free ATP, implying the presence of bacterial cells that have already died, which may hence serve as a kind of warning of possible contamination of the sample. The microbial extractant that will rupture the microbial cells present and will cause the ATP present to be released is added at time t=5. It can be inferred from FIGS. 10A and 10B that some of the microbial cells have released their ATP after 1 second (time t=6) already. It can also clearly be seen that the rates of release of the different microbial cells, as indicated by the inclination of the curve, differ. FIG. 10B clearly shows that the yeast "C. albicans" has a smaller inclination than all the tested bacteria, which was also already demonstrated above, in examples 1 and 2. It can also be seen that the inclination of the curve of "B. cereus" is greater than that of the curve of "G. stearophilus", whose inclination is in turn greater than that of the curve of "Cl. sporogenes". The process of the release of microbial ATP lasts until around time t=9 in the case of "G. stearophilus", t=10 in the case of "B. cereus", t=17 in the case of "Cl. sporogenes" and t=43 in the case of "C. albicans". The shapes of the curves of the different microbial cells moreover differ.

The type of microbial cells concerned can hence be inferred from the inclination, the duration of the release process and the shape of the curve. If a sample with an unknown contamination were to be measured it can on the basis of the curves shown in FIGS. 10A and 10B be determined which microbial cells it contains.

With the method according to the present invention it is possible to conduct a fast, accurate measurement of different types of microbial cells and to distinguish them into for example bacteria, yeasts and fungi, and also to distinguish between different types of bacteria and yeasts, for example between Gram-positive and Gram-negative bacteria, but also between different Gram-positive bacteria. With the method according to the present invention it is moreover possible to distinguish the amount of somatic ATP and the amount of microbial ATP, in addition to the amount of free extractant in products in a single sample.

Example 12

A hand lotion was suspended in water and a measurement as described in Example 1 was made, whilst also a "POS-BAC" sample was prepared by adding 50 µl of the culture of Example 1 with 20 ml of the suspension. Subsequently, a "NEG" sample and the "POS-BAC" sample were measured, and from the results (not shown) it appears that the contamination with bacteria can be clearly demonstrated.

Example 13

Example 12 was repeated, with the suspension being substituted for a 5 wt. % solution of acetylsalicylic acid in water. From the results (not shown) it appears that the contamination with bacteria can be clearly demonstrated.

What is claimed is:

1. A method for identifying the type of somatic cells that are present in a sample, said method comprising:
   (1) adding a somatic extractant to a sample suspected to be contaminated in order to release somatic ATP from a somatic cell;
   (2) adding a luminescence reagent to the sample from step (1) and measuring the luminescence of the ATP complex formed as a continuous function of time;

(3) calculating the rate at which ATP is released from the somatic cell based on the luminescence measured as a continuous function of time in step (2); and (4) comparing the rate of ATP released in step (3) to one or more reference values for rates of release of ATP from somatic cells;

wherein if the value for the rate in step (3) corresponds to the reference value, the sample and reference contain the same type of somatic cell.

2. The method according to claim 1 wherein the reference values for rates of release of ATP are obtained from standard curves for different types of somatic cells.

3. The method according to claim 1, wherein the luminescence is measured for a period of at least 10 seconds.

4. The method according to claim 1, the luminescence is measured for a period of at least 20 seconds.

5. The method according to claim 1, wherein the luminescence is measured for a period of at least 60 seconds.

6. A method for identifying the type of microbial cells that are present in a sample, said method comprising:

(1) adding a microbial extractant to a sample suspected to be contaminated in order to release somatic ATP from a somatic cell;

(2) adding a luminescence reagent to the sample from step (1) and measuring the luminescence of the ATP complex formed as a continuous function of time;

(3) calculating the rate at which ATP is released from microbial cells based on the luminescence measured as a continuous function of time in step (2); and (4) comparing the rate of ATP released in step (3) to one or more reference values for rates of release of ATP for microbial cells;

wherein if the value for the rate in step (3) corresponds to the reference value, the sample and reference contain the same type of microbial cell.

7. The method according to claim 6, wherein the reference values for rates of release of ATP are obtained from standard curves for different types of microbial cells.

8. The method according to claim 6, wherein the luminescence is measured for a period of at least 10 seconds.

9. The method according to claim 6, the luminescence is measured for a period of at least 20 seconds.

10. The method according to claim 6, wherein the luminescence is measured for a period of at least 60 seconds.

\* \* \* \* \*